United States Patent
Miklos et al.

(10) Patent No.: US 8,534,129 B2
(45) Date of Patent: Sep. 17, 2013

(54) PHOTOACOUSTIC MULTIPASS CELL WITH CONCENTRATING REFLECTION MEANS

(75) Inventors: Andras Miklos, Stuttgart (DE); Judit Angster, Stuttgart (DE)

(73) Assignee: Fraunhofer-Gesellschaft zur Foerderung der Angewandten Forschung E.V., Munich (DE)

( * ) Notice: Subject to any disclaimer, the term of this patent is extended or adjusted under 35 U.S.C. 154(b) by 726 days.

(21) Appl. No.: 12/593,177

(22) PCT Filed: Mar. 27, 2008

(86) PCT No.: PCT/EP2008/002438
§ 371 (c)(1),
(2), (4) Date: Sep. 25, 2009

(87) PCT Pub. No.: WO2008/116658
PCT Pub. Date: Oct. 2, 2008

(65) Prior Publication Data
US 2010/0107733 A1 May 6, 2010

(30) Foreign Application Priority Data

Mar. 27, 2007 (DE) .................. 10 2007 014 518

(51) Int. Cl.
*G01H 9/00* (2006.01)
(52) U.S. Cl.
USPC .............................................. 73/643; 73/596

(58) Field of Classification Search
USPC ............ 73/643, 24.02, 24.06, 579, 597, 596, 73/632; 356/301; 359/346, 347
See application file for complete search history.

(56) References Cited

U.S. PATENT DOCUMENTS

| | | | | |
|---|---|---|---|---|
| 4,269,509 | A * | 5/1981 | Berry et al. | 356/301 |
| 5,173,749 | A * | 12/1992 | Tell et al. | 356/437 |
| 5,615,043 | A * | 3/1997 | Plaessmann et al. | 359/346 |
| 7,069,769 | B2 * | 7/2006 | Kung | 73/24.02 |
| 7,263,871 | B2 * | 9/2007 | Selker et al. | 73/24.02 |
| 7,765,871 | B2 * | 8/2010 | Riddle | 73/590 |
| 7,861,574 | B2 * | 1/2011 | Sheen et al. | 73/24.02 |
| 2006/0123884 | A1 | 6/2006 | Selker et al. | |
| 2010/0103425 | A1 | 4/2010 | Miklos et al. | |
| 2010/0107732 | A1 | 5/2010 | Miklos et al. | |

FOREIGN PATENT DOCUMENTS

| | | |
|---|---|---|
| WO | 2004/008112 | 1/2004 |
| WO | 2004/008113 | 1/2004 |

OTHER PUBLICATIONS

Miklos et al. Application of a wavelength-amplitude double-modulation method in photoacoustic detection using a pulsed optical parametric oscillator; Journal de Physique IV France (2005) 579-581.

(Continued)

*Primary Examiner* — J M Saint Surin
(74) *Attorney, Agent, or Firm* — Greenblum & Bernstein, P.L.C.

(57) ABSTRACT

A photoacoustic multipass cell includes a light source, an acoustic resonator and a reflecting arrangement configured in a concentrating manner for reflecting light into the acoustic resonator. Additionally, the light source is arranged at least partially within the reflecting arrangement.

17 Claims, 2 Drawing Sheets

(56) References Cited

OTHER PUBLICATIONS

A. Miklos et al. "Multipass acoustically open photoacoustic detector for trace gas measurements," Applied Optics 45, 2529-2534, (2006).

Miklos A et al. "Application of acoustic resonators in photoacoustic trace gas analysis and metrology" vol. 72 No. 4, Apr. 1, 2004, pp. 1937-1955, XP012039066, ISSN: 0034-6748.

Lars-Goran Rosengren "Optical optoacoustic detector design" Applied Optics, vol. 14, No. 8/Aug. 1, 1975, pp 1960-1976, XP002456456, ISSN: 0003-6935.

Miklos A et al. "Windowless Resonant Acoustic Chamber for Laser-Photoacoustic Applications" Applied Physics B. Photophysics and Chemistry, Springer Verlag. Heidelberg, DE, vol. B48, No. 3, Mar. 1, 1989, pp. 213-218 XP000035737 figure 1.

German Office Action in the corresponding German application and partial English-language translation of the German Office Action, Oct. 29, 2007.

\* cited by examiner

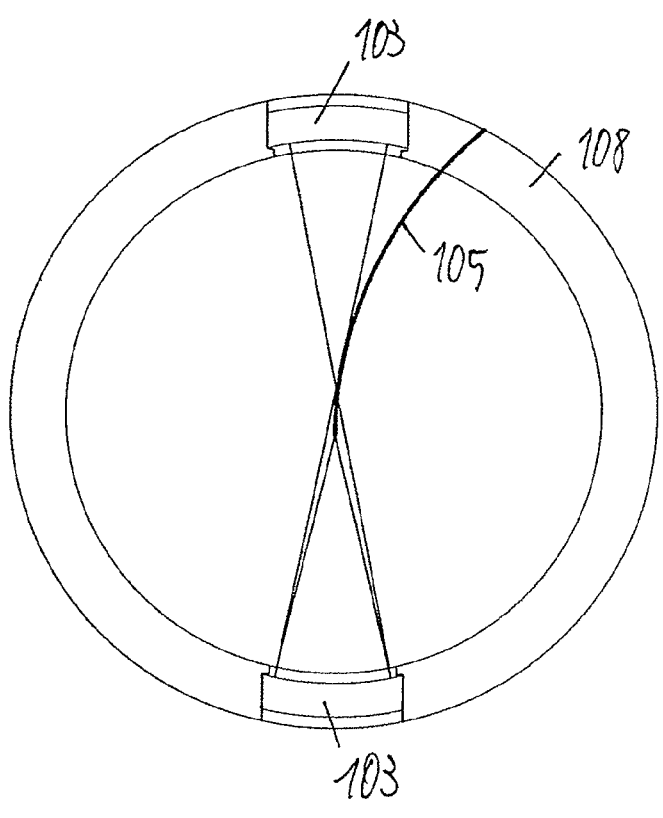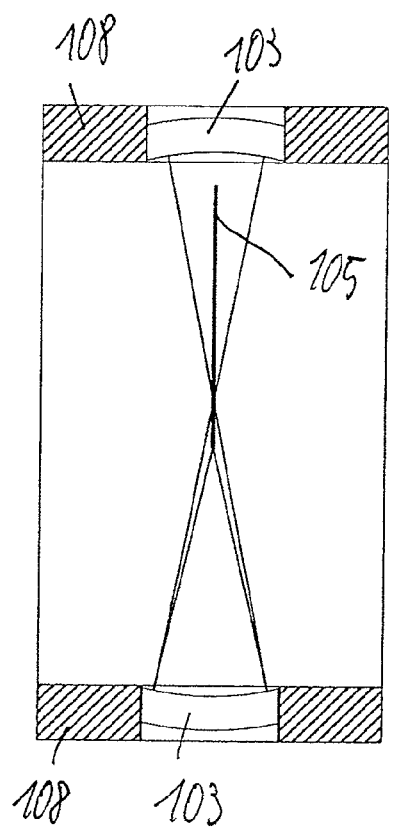
Fig. 2a
Fig. 2b

PHOTOACOUSTIC MULTIPASS CELL WITH CONCENTRATING REFLECTION MEANS

CROSS REFERENCE TO RELATED APPLICATIONS

The present application is a U.S. National Stage of International Application No. PCT/EP2008/002438 filed Mar. 27, 2008, which published as WO 2008/116658 A1 on Oct. 2, 2008, the disclosure of which is expressly incorporated by reference herein in its entirety. Further, this application claims priority under 35 U.S.C. §119 and §365 of German Application No. 10 2007 014 518.9 filed Mar. 27, 2007.

BACKGROUND OF THE INVENTION

1. Field of the Invention

The invention relates to a photoacoustic multipass cell in which the excitation light is provided by a divergent light source and is reflected multiple times. The divergent light source is generally formed by the suitably shaped end of an optical fiber.

2. Background Description

Photoacoustic measuring methods, i.e., measuring methods in which the substance to be investigated, preferably a gas, is irradiated with a light source and heated by absorption, are highly suitable for precisely measuring the concentration of absorbent gases or absorbent substances in gases. The gas expands when it is heated. If heating, and hence, expansion are periodic, a sound wave forms that can be measured by a sound pressure sensor. Photoacoustic spectroscopy has numerous advantages over classic absorption spectroscopy in which the light passing through the sample is measured, and the absorption is determined from the difference between the incident light and the light passing through the sample. The photoacoustic signal is linear within a concentration range of approximately 5-6 orders of magnitude. Sensitive photoacoustic cells can also be realized by using optical cells known from the prior art. Light is thereby generated in a light source and introduced into the optical cell. Usually, the light source is outside, and the light is conducted through an optical fiber into the optical cell. By suitable optical elements, the light can be guided into the optical cell as a parallel beam or focused beam. Cells known from absorption spectroscopy can be used as the sensitive optical absorption cells. The light is thus generally reflected several times in the optical cell. The multiple passage of the light allows the light to be absorbed well by the absorbent substances in the cell. Finally, the light leaves the cell and reaches a detector in which the light intensity is measured. When the light path is known, the absorption can be inferred using the Beer-Lambert law by comparing the incident light intensity and the intensity after light has passed through the cell several times. If an optical multipass cell of this type is modified such that the optical detector is omitted and sound pressure sensors are arranged instead, a photoacoustic multipass cell is achieved. A disadvantage of photoacoustic multipass cells of this type, however, is their relatively low sensitivity due to a high volume; generally, the volume is at least one-half liter. High sensitivity can be achieved with a photoacoustic multipass cell with a concave mirror installed. Experiments and test measurements of a multipass cell have shown, however, that this construction makes extremely high demands on the precise angle of incidence of the laser radiation and the adjustment of the concave mirror. This is described by A. Miklos, J. Ng, P. Hess, A. H. Kung in "Application of a wavelength-amplitude double-modulation method in photoacoustic detection using a pulsed optical parametric oscillator," Journal de Physique IV, 125, 579-582, (2005) and A. Miklos, S-C. Pei and A. H. Kung in the "Multipass acoustically open photoacoustic detector for trace gas measurements," Applied Optics 45, 2529-2534, (2006).

SUMMARY OF THE INVENTION

The aim of the present invention is therefore to overcome the disadvantages of the prior art and provide photoacoustic multipass cells that are very sensitive and do not require particularly precise adjustment of the exciting light beam.

This aim is attained by a photoacoustic multipass cell having a light source and an arrangement configured in a concentrated manner for reflecting light in an acoustic resonator, wherein the light source is arranged between the arrangement configured in a concentrated manner.

The dependent claims disclose advantageous developments.

Photoacoustic multipass cells are proposed having a light source and an arrangement for providing a high power density of light in an acoustic resonator. The arrangement for providing high power density of light reflects and concentrates the light, and is consequently configured in a concentrated manner. The light source is thereby arranged between the arrangement configured in a concentrated manner.

It was found that it is quite sufficient to ensure that the introduced light does not leave the photoacoustic multipass cell. The precise knowledge of the light path is irrelevant in photoacoustics. In particular, it is not necessary to conduct the light out of the multipass cell into an optical detector. That is, with optical multipass cells, the desired knowledge of the precise light path, the avoidance of interference and the requirement of conducting the light into an optical detector have meant that the reflectors cannot be designed in a concentrating manner, and therefore, must be adjusted very precisely. Even a slight misadjustment of a mirror or deviation of the angle of incidence of the light into the multipass cell results in the light not following the desired path in the multipass cell, but leaving the measuring area.

In contrast to optical multipass cells, since the photoacoustic signal is proportional to the light output absorbed in the multipass cell but independent of the absorption path, a photoacoustic multipass cell can be easily constructed such that the introduced light remains in the multipass cell and is concentrated in the acoustic resonator. The multiple reflection of a divergent light beam in the multipass cell leads to a substantial increase in the light output in the acoustic resonator.

The arrangement shown by A. Miklos, J. Ng, P. Hess, A. H. Kung in "Application of a wavelength-amplitude double-modulation method in photoacoustic detection using a pulsed optical parametric oscillator," Journal de Physique IV, 125, 579-582, (2005) includes a photoacoustic multipass cell having a light source between a reflection arrangement configured in a concentrated manner in an acoustic resonator. This arrangement already reduces the requirements for precisely adjusting the light source in comparison to the known optical multipass cells. However, the requirements still remain to couple the light from an external light source through a window into the multipass cell. Demands on the adjustment therefore still remain. However, if the light source is located between the arrangement configured in a concentrated manner, it is sufficient to ensure only that the light exiting the light source reaches the concentrating arrangement and is then reflected several times in the multipass cell. The light may thus exit the light source in a divergent manner.

The arrangement of the light source between the light-reflection arrangement configured in a concentrated manner results in an avoidance of conducting the light through windows into the acoustic resonator. Even if windows with a very high transmittance are used hereby, a certain amount of absorption still remains that leads to an undesirable photoacoustic background signal that systematically distorts the measurement. Except for the actual light-emitting surfaces, the light source can be coated with highly reflective materials or can be already constructed thereof so that the undesirable photoacoustic signal can be very small.

In the case of an excitation with a laser pulse, an effective extension of the excitation pulse can be carried out. With regard to acoustic times, however, this pulse extension is negligibly small. If the reflection arrangement has a spacing of 10 cm, the light requires approximately 0.33 ns to reflect. The number of reflections depends on the reflectivity of the reflection arrangement. If the reflectivity r is, for example, r=0.95, the pulse is obliterated after approximately 100 reflections. The pulse duration is thereby extended by 33 ns. Given a reflectivity of r=0.98 such as can be achieved with a gold-coated mirror, the pulse duration is extended by approximately 80 ns. The excitation pulse is amplified by a factor of $1/(1-r)$.

Given the low requirements for the light source, the light source can be designed in points. The spatial expansion can thus be very small, which prevents undesired absorption that would cause a background signal.

One suitable realization of the light source is a fiber guided into the photoacoustic multipass cell, at the end of which fiber the light from the fiber can reach the photoacoustic multipass cell. The above-described construction is advantageous especially when fibers are used. Light always emerges from fibers in a divergent manner. This divergence is generally acceptable with the device presented here. That is, in contrast to the prior art, it is not necessary for the light introduced into the multipass cell to be a parallel beam. For example, the reflection arrangement can easily be designed such that an emergence angle of up to approximately 26° from the fiber is acceptable.

It is also possible to use a laser diode arranged in the photoacoustic multipass cell as the light source. This layer diode is preferably to be provided with a lens. Depending on the divergence of the laser diode, the lens can be dispensed with in certain circumstances in view of the advantageous optical design. In any case, it is much easier in comparison to the prior art when the adjustment of the light source is less important.

Two spherical mirrors with a common optical axis are a suitable arrangement for reflecting the light. In this manner it is easily ensured that the light remains in the measuring range between the mirrors.

The two mirrors preferably have the same radius. This is optically favorable. It is thus also easily possible to arrange the mirrors such that they share a common midpoint. In addition, it is generally advantageous to use the same components, since larger quantities and consequently lower prices are thus possible.

The light source is preferably closer to the common midpoint of the mirrors than to one of the mirrors. Thus, the precise adjustment of the light source is particularly unimportant. Each light beam from the light source that strikes one of the mirrors remains in the area between the mirrors.

In a preferred embodiment, the acoustic resonator or the photoacoustic cell is designed as a cylinder. A cylinder is a body that is easy to provide, has good acoustic properties, and the gas to be investigated can easily flow through it. Depending on the guidance of the excitation light, it is thus also possible to excite the first longitudinal resonance, the first or second azimuthal resonance, or the first radial resonance of the cylindrical acoustic resonator.

An acoustic resonator is particularly advantageous in which the reflection arrangement is affixed to the side walls of the cylinder such that the sound wave that is best excitable by absorption of the excitation light is the second azimuthal resonance of the cylinder oscillation. To illustrate, let us consider a cylinder in cross section. If it is achieved through suitable excitation that expansions occur in opposite areas of the circle that represents the cylinder cross section, whereas no expansion occurs in the areas adjacent to the opposite areas that again lie opposite one another, a corresponding sound wave is achieved. Through the excitation circle segments with a pressure increased by the expansion are thus formed. The adjacent circle segments, which are larger, exhibit normal pressure, not elevated pressure. A circulating sound wave can form in the cylinder due to these differences in pressure. By suitably selecting the excitation frequency, i.e., the repetition frequency or modulation frequency of the light source, the second azimuthal resonance can be excited. This results in a high amplification of the photoacoustic signal.

A preferred embodiment has two opposing, spherical mirrors with a common midpoint. A divergent light source is arranged in the area of the common midpoint of the mirrors so that the excitation light can be guided to the first mirror from which it can be reflected to the opposite, second mirror such that the light can be reflected several times between the opposing mirrors. The divergent light source is generally formed by the end of a fiber. An excitation can thus be carried out with a simple device in the circle segments that lie between the mirrors. No heating occurs in the other area of the cylinder since light does not irradiate these areas.

The excitation light can be provided as an individual pulse or as a periodic sequence of pulses. When individual pulses are used for excitation, an oscillation develops in the photoacoustic multipass cell with the resonant frequency of the cell, preferably with the strongest resonant frequency. If with a periodic sequence the resonant frequency of the resonance excited or to be excited is selected as the pulse repetition frequency, a resonant oscillation likewise results. It should be noted that the resonant frequency generally depends on temperature. For this reason, excitation using single pulses is frequently preferable, since no adjustment to changing resonant frequencies is required.

A superior measuring system can be designed with the photoacoustic multipass cell.

BRIEF DESCRIPTION OF THE DRAWINGS

The invention is described in more detail below with reference to an exemplary embodiment without restricting the general application.

FIGS. 2a and 2b shows front and longitudinal cross-sectional views of a corresponding cylindrical photoacoustic multipass cell.

DETAILED DESCRIPTION OF THE INVENTION

Figure 1:
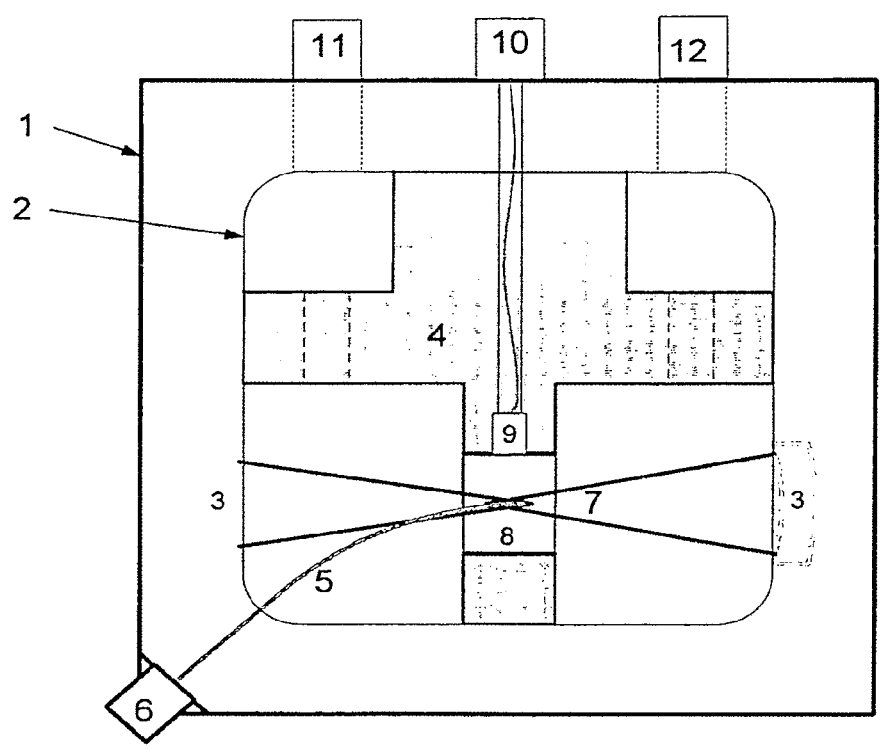
FIG. 1 thereby shows a possible design of a photoacoustic multipass cell.

As shown in FIG. 1, a cavity 2 is milled into a rectangular metal block 1. Two gold-coated, spherical mirrors 3 are arranged flush with the walls of the cavity 2. The cavity 2 is divided in turn into four smaller cavities. A body 4 of plastic is used for this. The light is guided into the cavity 2 through an optical fiber 5. This fiber 5 is encased in a metal capillary. The free end of the optical fiber 5 is arranged close to the common midpoint of the two spherical mirrors 3. The light leaving the fiber 5 strikes the mirror 3 located on the right in the drawing. The light source, a diode laser or quantum cascade laser, is connected to the photoacoustic detector by the fiber connection 6. The light beam striking the mirror 3 is reflected to the opposite mirror 3 and from there it is reflected back again. In each reflection, the light is concentrated towards the common optical axis of the mirror. The lines 7 indicate the limit up to which the area irradiated by light extends. The cylindrical acoustic resonator 8 is installed in the plastic body 4. The lower cavities are connected in this manner. The light can shine through the resonator 8 without striking the walls of the resonator 8. This prevents the walls from absorbing the light, and thus, generating an undesirable photoacoustic signal. A measuring microphone 9 serving as the sound pressure sensor is attached to the metal wall of the acoustic resonator 8. The measuring microphone 9 is connected to the resonator 8 by a small hole (not shown in the drawing). The microphone 9 is connected to an electric plug 10 through a bore in the plastic body 4. This plug 10 is located at the edge of the metal block 1 and serves to connect an evaluation circuit that is conventional in photoacoustics. The gas to be investigated flows through the gas inlet 11 into the photoacoustic detector. It thereby flows through a hole in the plastic body 4 into the lower left cavity. From there, it the gas flows through the acoustic resonator 8 into the lower right cavity, and leaves the photoacoustic detector through another hole in the plastic body 4 and flows out again through the gas outlet 12. The photoacoustic multipass cell is covered with a metal plate (not shown). The seal between the metal plate and metal block 1 is provided by an O-ring (not shown) and the attachment by screws (not shown).

FIGS. 2a and 2b illustrate the excitation of the second azimuthal resonance of the cylinder oscillation in an acoustic resonator. Two opposing spherical mirrors 103 with a common midpoint are available for this purpose. A fiber 105 ends in the area of the common midpoint of the mirrors 103. The light exits in a divergent manner and strikes one of mirrors 103. From there it is reflected to the other mirror 103. Excitations occur in the area between the mirrors 103 due to multiple reflections. No excitation occurs in the other areas. Since the excitation light exits the fiber in a pulsed manner and the pulse repetition frequency corresponds to the second azimuthal resonance of the cylinder oscillation, this is primarily excited. A high signal is thus produced.

The photoacoustic cell 108 is thus designed as a cylinder.

LIST OF REFERENCE NUMBERS

1 Metal block
2 Cavity in the metal block
3 Gold-coated mirror
4 Plastic body
5 Optical fiber
6 Fiber connection
7 Border line of the irradiated area
8 Acoustic resonator
9 Measuring microphone
10 Plug
11 Gas inlet
12 Gas outlet
103 Mirror for cylindrical resonator
105 Fiber for cylindrical resonator
108 Cylindrical photoacoustic measuring cell

The invention claimed is:

1. A photoacoustic multipass cell comprising:
a light source;
an acoustic resonator; and
a reflecting arrangement configured in a concentrating manner for reflecting light into the acoustic resonator,
wherein the light source is arranged at least partially within the reflecting arrangement.

2. The photoacoustic multipass cell according to claim 1, wherein the light source comprises a fiber guided into the photoacoustic multipass cell, such that light from an end of the fiber is emitted in the photoacoustic multipass cell.

3. The photoacoustic multipass cell according to claim 1, wherein the light source comprises a laser diode.

4. The photoacoustic multipass cell according to claim 3, wherein the laser diode comprises a lens.

5. The photoacoustic multipass cell according to claim 1, wherein the reflecting arrangement comprises two spherical mirrors with a common optical axis.

6. The photoacoustic multipass cell according to claim 5, wherein the spherical mirrors each have a same radius.

7. The photoacoustic multipass cell according to claim 5, wherein the light source is arranged closer to a midpoint between the spherical mirrors then to one of the spherical mirrors.

8. The photoacoustic multipass cell according to claim 1, wherein at least one of the acoustic resonator and the photoacoustic multipass cell is structured as a cylinder.

9. The photoacoustic multipass cell according to claim 8, wherein the reflecting arrangement is attached to side walls of the cylinder such that a sound wave excitable by an absorption is a second azimuthal resonance of a cylinder oscillation.

10. A photoacoustic measuring system containing a photoacoustic multipass cell according to claim 1.

11. The photoacoustic multipass cell according to claim 1, wherein:
the reflecting arrangement comprises two opposing spherical mirrors with a common midpoint, and
the light source comprises a divergent light source arranged in an area of the common convergence point such that:
excitation light is guided to a first mirror of the two opposing spherical mirrors; and
excitation light from first mirror is reflected to the opposing second mirror,
such that the excitation light is reflectable multiple times between the two opposing spherical mirrors.

12. The photoacoustic multipass cell according to claim 9, wherein the excitation light is supplied with a modulated wavelength or modulated intensity, and wherein the frequency of a resonance excited is set as the modulation frequency.

13. The photoacoustic multipass cell according to claim 9, wherein the excitation light is supplied as a single pulse or a periodic sequence of pulses, wherein with the periodic sequence of pulses, a pulse repetition frequency corresponds to a resonant frequency of a resonance excited.

14. A method for investigating a gas in a photoacoustic multipass cell having an acoustic resonator, comprising:
reflecting excitation light from a light source in the acoustic resonator in a concentrating manner between two opposing spherical mirrors with a common convergence point, wherein the light source is arranged between the two mirrors.

15. The method of claim 14, wherein the reflecting the light comprises:
   guiding the excitation light from the light source to a first mirror of the two opposing spherical mirrors; and
   reflecting the excitation light from the first mirror to the opposing second mirror such that the excitation light can be reflected multiple times between the opposing spherical mirrors.

16. The method of claim 14, further comprising supplying the excitation light with a modulated wavelength or modulated intensity, wherein the frequency of a resonance excited is set as the modulation frequency.

17. The method of claim 14, wherein the excitation light is supplied as a single pulse or a periodic sequence of pulses, wherein with the periodic sequence of pulses, a pulse repetition frequency corresponds to a resonant frequency of a resonance excited.

* * * * *